United States Patent [19]

Ebisawa et al.

[11] Patent Number: 5,043,747
[45] Date of Patent: Aug. 27, 1991

[54] HEAD FOR INK SET RECORDING TREATED WITH AN INK-REPELLANT AGENT

[75] Inventors: Isao Ebisawa, Tokyo; Hiromichi Noguchi, Atsugi, both of Japan

[73] Assignee: Canon Kabushiki Kaisha, Tokyo, Japan

[21] Appl. No.: 497,329

[22] Filed: Mar. 22, 1990

[30] Foreign Application Priority Data

Mar. 24, 1989 [JP] Japan .................................... 1-70548
Mar. 15, 1990 [JP] Japan .................................... 2-62842

[51] Int. Cl.$^5$ ............................................ B41J 2/165
[52] U.S. Cl. .................. 346/140 R; 549/559; 560/140
[58] Field of Search ............... 346/140; 549/599, 598, 549/555; 560/140, 221, 81, 90

[56] References Cited

U.S. PATENT DOCUMENTS 4,368,476  1/1983  Uehara ............................... 346/140
4,922,019  5/1990  Lau ..................................... 564/332

FOREIGN PATENT DOCUMENTS 0295639  12/1988  European Pat. Off. .
0319919  6/1989  European Pat. Off. .
3047835  8/1981  Fed. Rep. of Germany .

OTHER PUBLICATIONS

Patent Abstracts of Japan, vol. 11, No. 85 (C-140) (2532), JP-A-61238761.

*Primary Examiner*—Joseph W. Hartary
*Attorney, Agent, or Firm*—Fitzpatrick, Cella, Harper & Scinto

[57] ABSTRACT

A head for ink jet recording and an ink jet recording apparatus equipped with this head, wherein the head has an end face that includes an ink eject opening having a thin layer of a polymer derivative compound of 1,3- or 1,4-bis(hexafluoroisopropyl)benzene, or 2,2-disphenylhexafluoropropane represented by the formula (I or II):

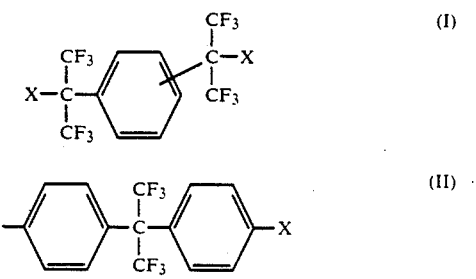

wherein X represents

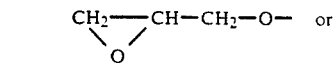

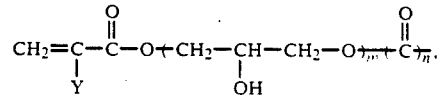

Y represents hydrogen atom or methyl group, m and n represent 0 or 1, and when m is 0, n is also 0.

14 Claims, 5 Drawing Sheets

HEAD FOR INK SET RECORDING TREATED WITH AN INK-REPELLANT AGENT

BACKGROUND OF THE INVENTION

1. Field of the Invention

This invention relates to a novel derivative compound of 1,3- or 1,4-bis(hexafluoroisopropyl) benzene, or 2,2-bisphenylhexafluoropropane to be used for ink-repellent treatment, an ink-repellent agent containing such compound, a head ink jet recording coated on ink eject opening end surface with such ink-repellent agent, and an ink jet recording device equipped with such head.

2. Related Background Art

With propagation of computers in recent years, various application instruments have been actively developed. Particularly, remarkable progress can be seen in developement and propagation of office instruments for office automation such as copying machines, facsimiles, word processers and other so called personal computers, etc.

In these office instruments, the so called printer as the instrument for output of the processed data or sentences, etc. is an essential device.

In the prior art, as such printer, there have been employed a printer of the impact system such as wire dot printer, etc., a laser beam printer by use of the electrostatic copying system, a printer of the non-impact system such as heat transfer printer, etc., but a printer of the ink jet recording system is attracting attention in recent years because of its excellent characteristics, and developements of various systems are now under progress.

It is of course desirable that printing and images by a printer should be beautiful and precise, and the target of these printer techniques resides here. As a means for that purpose, one may consider to make ink eject nozzles smaller and arrange them closely to each other. For that purpose, there has been known the method in which a large number of eject openings are prepared closely to each other by use of the fine working system using the so called microlithographic technique.

FIG. 7 shows a constitutional example of an ink jet recording head of the prior art prepared according to such method. In FIG. 7, 71 is a first substrate formed of, for example, a silicon wafer, etc., 72 a layer formed of, for example. $SiO_2$, etc. on the surface of the first substrate 1. 73 is a nozzle wall formed by such method as lithography, etc., 74 a second substrate formed of, for example, a glass plate, 75 an adhesive layer for adhering the second substrate 74 to the upper part of the nozzle wall 73, and 76 an ink eject opening of nozzle. Such recording is worked very precisely with the nozzle wall 73 being made to have dimensions of 25 $\mu$m of height and 20 $\mu$m of width, and the ink jet eject opening 76 to have the same dimensions as the nozzle wall 73.

FIGS. 8A and 8B show side sectional views of the ink jet recording head shown in FIG. 7, showing two examples under the state of forming ink droplets 88 by ejecting of the ink 87. FIG. 8A shows the state in which ink droplets are ejected straightforward without wetting of the eject opening end surface 89 with ink, while FIG. 8B shows the state in which ink droplets are going to be ejected slant, because a part of the eject opening end surface 89 is wetted with ink before ejecting.

The ejecting opening end surface 89 may be wetted and spread with ink during ink ejecting, or otherwise sometimes in a device in the form of performing recording with the recording head mounted on a carriage, the ink 87 within the nozzle may be overflowed outside from the eject opening end surface 89 to wet that portion by mechanical vibrations, caused by mechanical movement of the head when it performs printing, or when it returns again to home position after reaching of the carriage to the end of the recording medium.

Thus, when the ink overflowed to wet the eject opening end surface 89 is returned again within the eject opening, or when the peripheral portion of the eject opening is uniformly wetted, the eject direction of the ink droplets 88 becomes straight as shown in FIG. 8A, whereby the ejecting state, namely the recording state is stabilized.

However, in the ink jet recording head of the prior art, due to differences in wettability between the second substrate 74 and the adhesive layer 75, the eject opening end surface 89 may be wetted nonuniformly, or as shown in FIG. 8, nonuniform residual state of ink occurs on the eject opening end surface 89 after once wetted, whereby unstable ejecting state as shown in FIG. 8B occurs.

Thus, there is a strong relationship between wetting of the eject opening end surface and the surface state of the end surface, and when the surface state of the eject opening end surface is not adequate, an unstable ejecting state occurs, whereby a good recording state cannot be maintained, lowering the recording quality.

This is also a problem which occurs as a matter of course not only in the ink jet recording head of the constitution shown in FIG. 7 but also generally in an ink jet recording head which has an ink ejecting nozzle formed smaller and is adapted to perform ink ejecting at high velocity and high frequency. However, particularly in the case as in the ink jet recording head shown in FIG. 7, when ink eject openings are provided closely to each other, since wetting occurs around the eject openings adjacent to each other, wetting is connecting mutually between the adjacent eject openings, and its influences become increasingly greater. As the result, further remarkable adverse influences such as deformation of recorded letters or disturbance of the images may be exerted on recording quality or images, and therefore it is necessary to manage the eject opening end surface more strictly.

In the prior art, for the purpose of maintaining ink ejecting stability of an ink jet recording head, there have been made various proposals of performing an ink repellent treatment which is the surface treatment of the head surface.

As an example, as disclosed in Japanese Patent Laid-open No. 63-122560, there have been proposed the method in which removeable solids are filled internally of the eject opening to form a thin layer of an ink-repellent agent on the surface of an elastic member, and the thin layer is transferred onto the surface at the peripheral portion of the eject opening of the recording head, or as desclosed in Japanese Patent Laid-open No. 63-122557, the method in which while a gas is jetted out through eject openings, the recording head end surface having said eject openings is dipped in an ink-repellent agent.

Among such proposals, for enhancing the effect of the ink repellent treatment used, there has been frequently used a substance having many fluorine atoms (see Japanese Patent Laid-open Nos. 63-122550, 63-122557, 63-122559, 63-122560, etc.).

For example, as the treating agent which makes the eject opening end surface liquid-repellent, Japanese Patent Laid-open No. 56-89569 discloses use of undecafluoropentyltrimethoxysilane, tridecafluorohexyltrimethoxysilane, perfluorodecyltrimethoxysilane, 1,1,2,2-tetrafluoroethyltrichlorosilane, pentafluorophenyldimenthylchlorosilane, 2,2,3,3-tetrafluorocyclobutyl, etc.

Moreover, KP 801 (Shinetsu Kagaku, trade name) which is a perfluoroalkylsilicone type water-repellent agent or a photocurable type fluorine type liquid resin, such as DEFENSA (DIC, trade name), etc., which is diluted with Daifuron (DAIKIN KOGYO, trade name), etc. is coated in a thin film on an elastic support such as silicone rubber, etc., and after evaporation of the solvent, the film is transferred onto the recording head surface to form an ink-repellent film.

On the other hand, in an ink jet recording device, water contained in ink or recording medium may be evaporated to make the atmosphere of the recording head highly humid, and depending on the conditions such as the temperatures of the recording head or in the atmosphere, etc., dew formation may sometimes occur on the ink jet ejecting surface.

also, splashed ink from the recording medium. may also wet the ink ejecting surface.

The phenomena such as dew formation, wetting as mentioned above become more conspicuous in the case of using a fixing heater for accelerating fixing of the recorded image onto a recording medium or in the case when the dot duty of the recorded image is high.

Thus, when dew formation or wetting has occurred on the ejecting surface, the ejecting surfaces becomes attached nonuniformly with water droplets, etc., and these attached water droplets will attract nonuniformly the ejected ink when the ink is ejected through eject openings. As a result variances occur in ejecting directions of ink, ejecting rate and also in ink droplet diameters, whereby lowering in recording quality will be brought about. Also, due to wetting of the ejecting surface, paper powder, dust, etc. are readily attached thereon, and these may have adverse influences on the ink ejecting direction of ink, etc., or cause clogging of the eject openings to occur, whereby lowering of recording quality may be caused.

As a measure to cope with such troubles, it has been practiced to remove dew formation, wetting, etc., by wiping the ejecting surface at predetermined timing.

For example, by use of a blade comprising a silicone rubber, etc., as the wiping means, the blade is engaged with the ejecting surface as accompained with the movement of the recording head, thereby wiping off water or dust, etc. of dew formation, wetting, etc.

The fluorosilicone type ink-repellent agent of the prior art, although excellent in the ink-repellent effect, tended to be weaker to the abrasion force from outside accompanied with the wiping actuation. The principal cause for these tendencies resided in use of a substance having a long aliphatic chain as represented by $-C_8F_{17}$, etc.

Also, it has been found that the ink-repellent agent is abraded by a wiper to be markedly deteriorated when printing is performed with the head being maintained at a relatively higher temperature (40° to 50° C.).

SUMMARY OF THE INVENTION

Accordingly, an object of the present invention is to provide a novel compound to be used for an ink-repellent agent which increases the abrasion resistance strength of the above-mentioned ink-repellent agent, and at the same time does not lower the ink repellent treating effect, and an ink-repellent agent containing the same.

Specifically, its object is to prevent damaging or abrasion of the ink-repellent film by the wiper actuation of an elastic member such as rubber, etc. provided for the purpose of removing dust or ink attached on the head surface.

Also, still another object is to elevate the glass transition temperature (Tg) of the ink repellent agent for the purpose of preventing remarkable lowering in strength and abrasion acceleration due to softening of the ink-repellent agent by heat.

Still another object of the present invention is to provide a head for ink jet recording which enables constantly stable ink ejecting even when wiping actuation may be performed on the ejecting surface of ink, and an ink jet recording device equipped therewith.

The above objects can be accomplished by the present inventions as specified below.

In accordance with the present invention, there is provided a derivative compound of 1,3- or 1,4-bis(hexafluoroisopropyl)benzene, or 2,2-bisphenylhexafluoropropane represented by the formula (I) or (II):

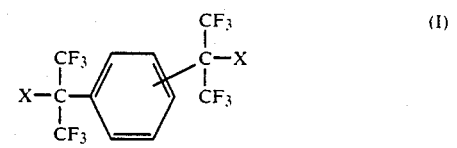 (I)

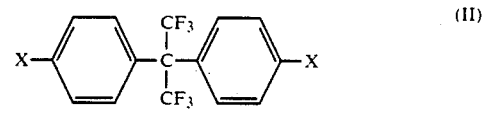 (II)

wherein X represents

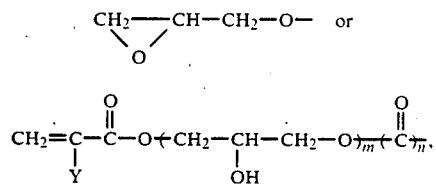

Y represents hydrogen atom or methyl group, m and n represent 0 or 1, and when m is 0, n is also 0.

The present invention also provides an ink-repellent agent comprising the above derivative compound represented by the formula (I) or (II).

Futher, the present invention provides a head for ink jet recording comprising an end face including an ink jet opening having a thin layer of polymer comprising the above derivative compound represented by the formula (I) or (II).

Further, the present invention provides an ink jet recording device, having a recording head equipped therein, said recording head comprising an end face including an ink eject opening having a thin layer of polymer comprising the above-derivative compound represented by the formula (I) or (II).

DETAILED DESCRIPTION OF THE PREFERRED EMBODIMENTS

Figure 1:
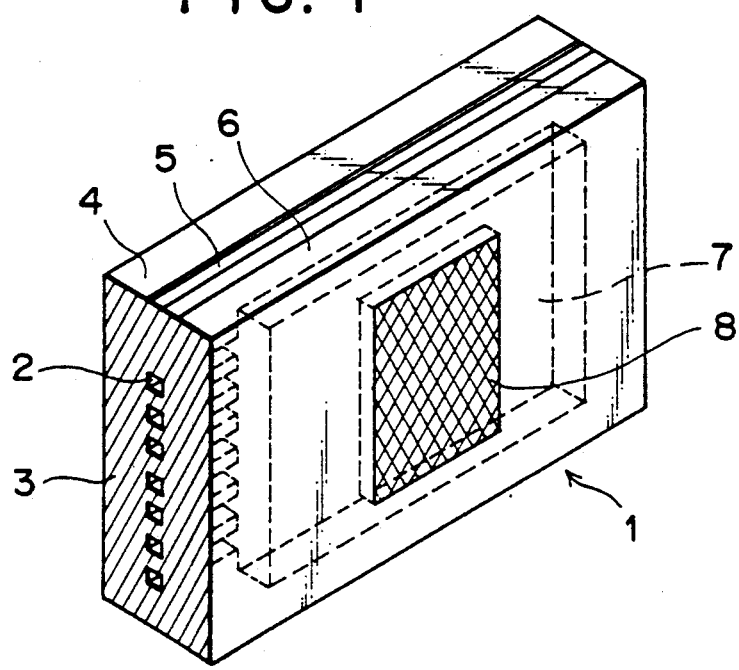
FIG. 1 is a perspective view showing the state of a head when coated with the ink-repellent agent of the present invention.

By use of compound represented by the above formula (I) OR (II) as the ink-repellent agent, abrasion resistance strength can be remarkably improved without lowering the ink-repellent effect of the ink-repellent film.

In the present invention, as the derivative compound to be used for the ink-repellent agent, a compound containing at least one benzene ring and 6 or more fluorine atoms, and also having 2 or more (meth)acryloyl groups or gylcidyl groups as represented by the above formula is used.

The above-described compounds of the present invention have been synthesized from a bifunctional compound which is excellent in ink repellency and rigid in molecular structure as the starting material, by adding (meth)acryloyl or glycidyl groups thereto to make them the UV reaction type or the thermosetting reaction type.

Preferable specific examples of the bifunctional compound which is excellent in ink repellency and rigid in molecular structure may include those having the following structures:

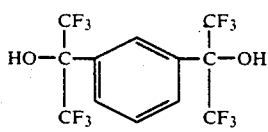
(A)

[1.3-bis(2-hydroxy hexafluoro isopropyl)benzene]

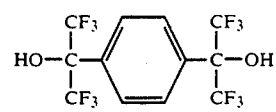
(A')

[1,4-bis(2-hydroxy hexafluoro isopropyl)henzene]

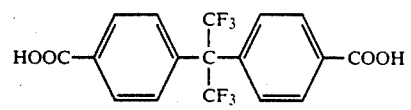
(B)

[2,2-bis(4-carboxyphenyl)hexafluoropropane]

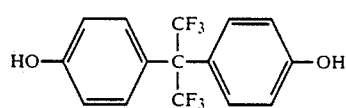
(C)

[2.2-bis(4-hydroxyphenyl)hexafluoropropane]

For example, by reacting a functional derivative such as (meth)acrylic acid or acid chloride thereof, etc, with the above starting material (A) or (C), it can be formed into an ink repellent agent of the UV reaction type as shown below.

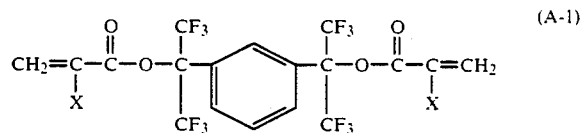
(A-1)

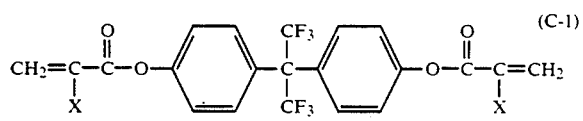
(C-1)

Also, by the reaction of epichlorohydrin with the starting material (A) or (C), substances shown below can be formed.

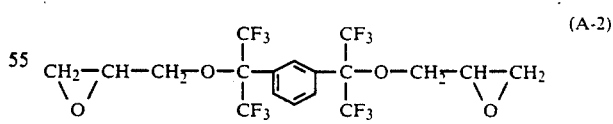
(A-2)

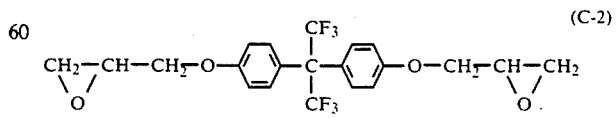
(C-2)

Also, by the reaction of glycidyl (meth)acrylate with the starting material (A) to (C), compounds represented by the following formulae can be formed:

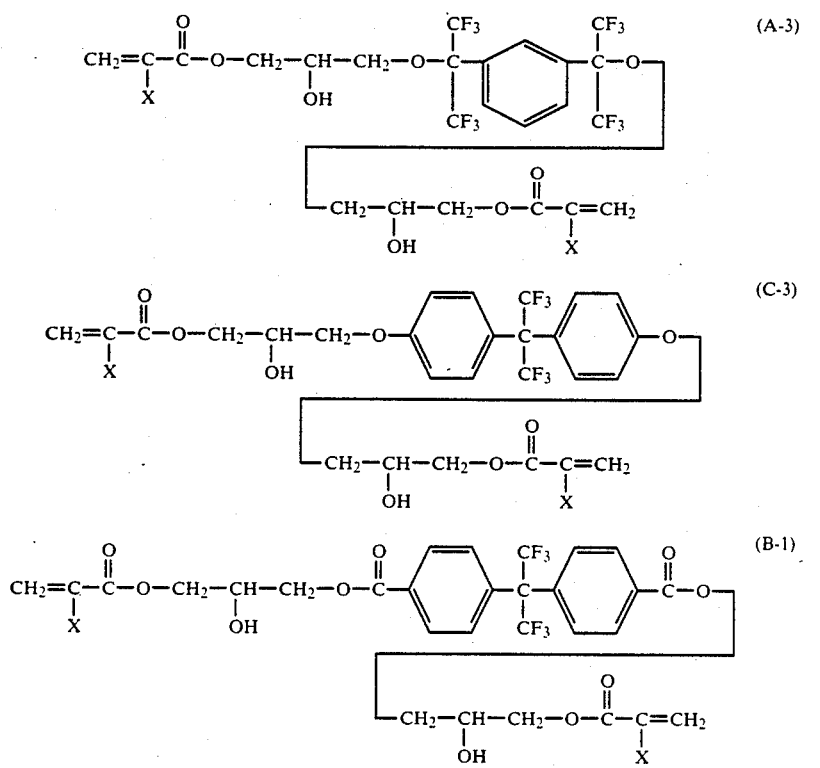

wherein X is a hydrogen atom or a methyl group.

Specific synthesis examples of the compounds as mentioned above are shown below.

Synthesis example of acrylate of 1,3-bis(2-hydroxy hexafluoro isopropyl) benzene (A)

82 g (0.2 mole) of 1,3-bis(2-hydroxy hexafluoro isopropyl)benzene were dissolved in 300 ml of hexafluoroxylene as the solvent, and the solution was elevated to 60° C. While stirring the reaction mixture, 45.2 g (0.5 mole) of acrylic acid chloride was slowly added dropwisely from a dropping funnel. The reaction was carried out at 60° C. for 3 hours, and after lowered to room temperature, the reaction mixture was thrown into a 2000 ml aqueous solution set at pH=12 with NaOH, followed by vigorous stirring. Subsequently, the phase of hexafluoroxylene was separated from the solution separated into two phases, and mixing with pure water and separation therefrom were repeated several times, thereby removing NaCl formed and the unreacted acrylic acid into aqueous phase. Then, hexafluoroxylene was distilled under reduced pressure to give an acrylated product of 1,3-bis(2-hydroxy hexafluoro isopropyl) benzene (A-1).

The reaction of 2,2-bis(4-carboxyphenyl)hexafluoropropane (B) with glycidyl methacrylate 196 g (0.5 mole) of 2,2-bis(4-carboxyphenyl)-hexafluoropropane were mixed with 500 g of toluene, 1.8 g of triethanolamine was added as the catalyst, and while stirring gently the mixture at normal temperature, 142 g (1 mole) of glycidyl methacrylate was added to the above mixture dropwisely over one hour. Subsequently, the temperature was raised to 65° C., and the reaction was further carried out for 3 hours. After completion of the reaction, toluene was removed under reduced pressure to give the reaction product (B-1) of 2,2-bis(4 4-carboxyphenyl)hexafluoropropane and glycidyl methacryalte.

The reaction of 2,2-bis(4-hydoxyphenyl) hexafluoro-propane (C) with eiphichlorohydrin 336 g (1mole) of 2,2-bis-(4-hydroxyphenyl)-hexafluoropropane and 833 g (9 moles) of epichlorohydrin were placed in a reaction flask, and the solution was heated under reflux to 120° C. Into the solution was added 203 g (2 moles) of an aqueous 40% by weight of NaOH solution dropwisely over 3 hours. The temperature during the dropwise addition was in the range from 99° to 119° C. Of the water and the epichlorohydrin distilled during the reaction, only the epichlorohydrin was returned to the reaction vessel. After excessive epichlorohydrin was recovered under reduced pressure after the dropwise addition of NaOH, 1000 ml of toluene was added, the mixture was washed three times with 1000 ml of water, and the NaCl formed and the residual alkali were removed. Finally, toluene was removed by evaporation under reduced pressure. As described above, the reaction product (C-8) of 2,2-bis(4-hydroxyphenyl)hexafluoropropane and epichlorohydrin was obtained.

This compound, when used alone, can form a rigid film of an ink-repellent agent, and also it is preferably used in a mixture with the substances used in the respective inventions of Japanese Patent Laid-open Nos. 63-122550, 63-122557, 63-122559 and 63-122560, or an ink-repellent agent containing a perfluoroalyl group of the $C_8H_{17}$ type widely used in the same kind of product, and the ink repellent effect can be also retained when used in a mixture to improve the strength of the film to great extent as compared with the ink-repellent agents of prior arts when used alone, whereby the objects of the present invention can be accomplished satisfactory.

Thus, by use in a mixture, it has been rendered possible to elevate Tg of the ink-repellent film comprising the mixture and increase the abrasion resistance strength to 5-fold of more of that of the prior art.

With respect to the ink-repellent property and abrasion resistance, the more preferable embodiment of the ink-repellent agent of the present invention is of the agent, which comprises both the derivative compound of the formula (I) or (II) and the liquid compound polymerizable with the derivative.

Such compounds which are liquid at room temperature are, for example, liquid epoxy compounds or liquid acrylic compounds.

The embodiment for the combination co-used for the present invention is as follows:

(1) the compounds having epoxy group at end of molecular chain of the formula (III) or (IV) and the liquid epoxy compounds.

(2) the compounds having acryloyl group at end of molecular chain of the formula (V) or (VI) and the liquid acrylic compounds.

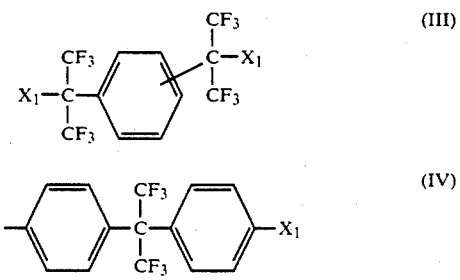
(III)

(IV)

wherein $X_1$ is

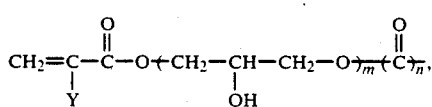

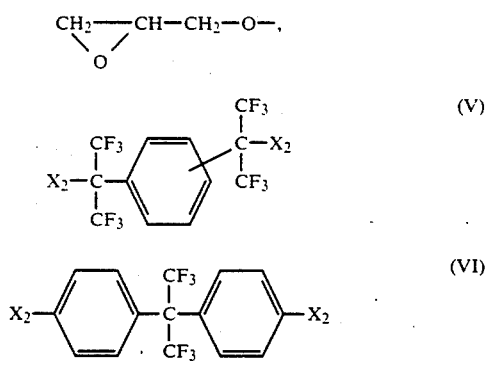
(V)

(VI)

wherein $X_2$ is $$CH_2=C-C-O+CH_2-CH-CH_2-O\overline{\phantom{x}}_m(C)_n,$$
$\quad\quad\quad|\quad\quad\quad\quad\quad\quad|$
$\quad\quad\quad Y\quad\quad\quad\quad\quad\quad OH$ Y is hydrogen or methyl, m and n are 0 or 1, and when m is 0, n is also 0.

As liquid epoxy compounds or liquid acrylic compounds, compounds containing no fluorine atom are more preferable for the present invention, as compared with compounds containing a fluorine atom, since they are excellent in contactivity with a head surface, film formability and abrasion resistance.

The preferable liquid epoxy compounds are liquid bisphenol type epoxy resins such as Epikote 825, 827, 828, 834, 807 (produced by Yuka Shell Epoxy Co.); liquid phenol novolac type epoxy resins such as Epikote 152, 154; cyclic aliphatic epoxy resins such as Ceroxide 2000, 3000 (produced by Daicel Kagaku Co.), CYRACURE UVR 6110, 6200 (produced by Union Carbide Co.); epoxy reactive diluents represented by phenyl glycidyl ether.

And liquid acrylic compounds are polyfunctional liquid acrylic oligomers having acryloyl groups at its end disclosed in Japanese Patent Laid-Open No. 1-290438 and are selected from liquid substances known as UV-curable resins, exemplified as follows:

(i) polyhydric acrylates derived from adding 2 or more (meth)acrylic acids to polyhydric alcohol, the polyhydric alcohols being, for example, ethyleneglycol, 1,6-hexanediol, trimethylolpropane, pentaerythritol, dipentaerithritol and so on;

(ii) polyesteracrylates derived from adding 2 or more (meth)acrylic acids to polyesterpolyols obtained from polyhydric alcohols and polybasic acids, the polyhydric alcohols being, for example, ethyleneglycol, 1,4-butandiol, 1,6-hexanediol, diethyleneglycol, trimethylolpropane, dipropyleneglycol, polyethyleneglycol, pentaerythritol, dipentaerithritol, the polybasic acids being, for example, phthalic acid, adipic acid, maleic acid, succinic acid, terephthalic acid, alkenyl succinic acid and so on;

(iii) epoxyacrylate, the functional group of which is acryloyl group derived from esterifying epoxy groups of epoxy resins with (meth)acrylic acid, the epoxy resins being, for example, of the types of bisphenol-A-epichloro-hydrine, phenol novolac-epichlorohydrine, aliphatic cyclic epoxy resins and so on;

(iv) polyurethane acrylates, obtained from reacting hydroxy(meth)acrylate with polyhydric isocyanates, the polyhydric isocyanates being, for example, compound having polyester, polyether and the like at the central part of the molecule and having isocyanates groups at the both ends and so on;

(v) the others, for example, polyetheracrylates, melamine-acrylates, alkylocrylates, isocyanurateacrylates, silicone acrylates and so on.

Such acrylates are examplified as follows:

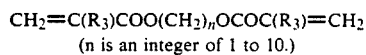   A-1
(n is an integer of 1 to 10.)

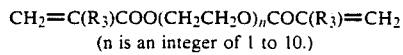   A-2
(n is an integer of 1 to 10.)

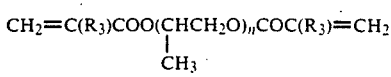   A-3
(n is an integer of 1 to 10.)

-continued
  A-4
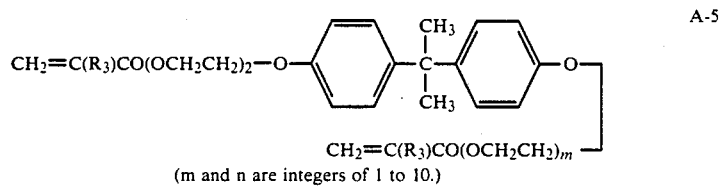  A-5
(m and n are integers of 1 to 10.)
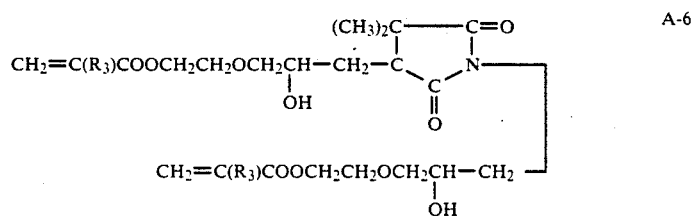  A-6
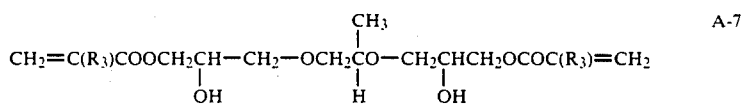  A-7
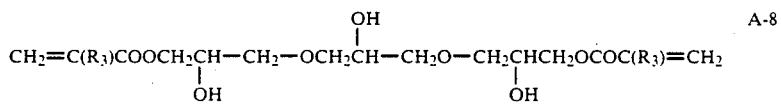  A-8
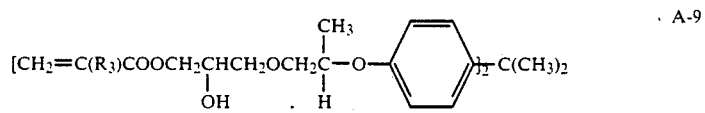  A-9
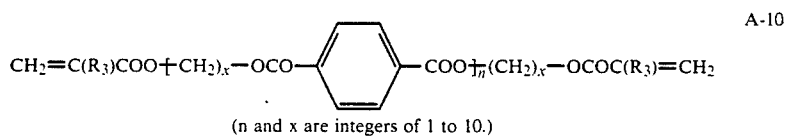  A-10
(n and x are integers of 1 to 10.)
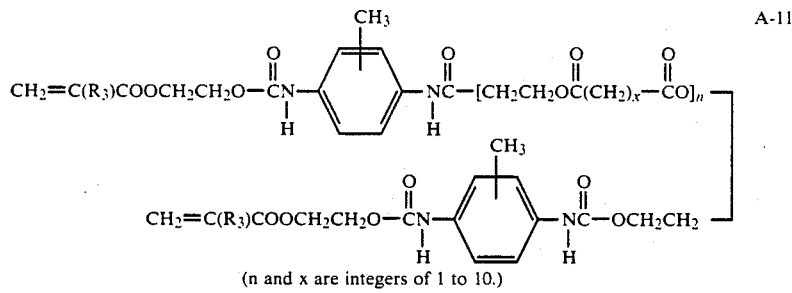  A-11
(n and x are integers of 1 to 10.)
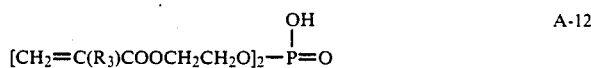  A-12
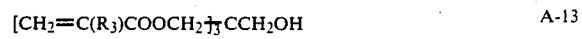  A-13
  A-14
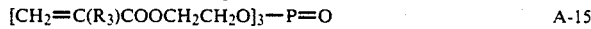  A-15
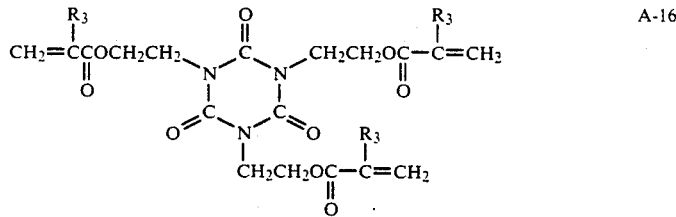  A-16

[CH$_2$=C(R$_3$)COOCH$_2$]$_4$—C     A-17
wherein R$_3$ is H or —CH$_3$.

Those liquid epoxy compounds or liquid acrylic compounds are good in compatibility when they are co-used with the compounds of the present invention, then isolation and precipitation do not cause.

In the case that the compounds of the present invention and the liquid compound are co-used, the compounds of the present invention are used not less than 30% by weight, preferably not less than 50% by weight, to the liquid compounds. In case of less than 30% by weight, the ink-repellent property may be lowered.

The ink-repellent agents of the present invention are used as follows:

In the case of compounds (III) and (IV) having epoxy groups at the chain end, the compounds (or the compounds and liquid epoxy compounds) are mixed with epoxy cure agent, diluted with coating solvents, coated on the head end surface and followed by heat curing. Or the compounds are mixed only with heatcure catalysts, photocure catalysts, diluted with coating solvents and coated on the nozzle surace and followed by curing treatment with active energy such as heat or ultraviolet light and the like. The epoxy cure agents shall mean known aromatic acid anhydrides, aliphatic amines, the heatcure catalysts shall mean imidazoles, aromatic amines, nitrils and photocure catalysts shall mean aromatic halonium salts, which generate a lewis acid by applying active energy light.

In the case of compounds (V) and (VI) having acryoyl groups at the chain end, the compounds (or the compounds and liquid epoxy compounds) are mixed with photocure catalysts, diluted with coating solvents, coated on the head end surface and followed by photocure treatment with active energy light. The photocure catalysts shall mean compounds such as benzoinalkylethers, benzophenones, anthraquinones, acetophenones and the other aromatic ketones, which generate radicals by applying active energy light. Good compatible compounds with the derivative compounds of the present invention or liquid compounds are preferably, for example, benzophenone, hydroxycyclohexylphenylketone (Irgacure 184, available from CIBA GEIGY Co.); 1-(4-iso-propylphenyl)-2-hydroxy-2-methylpropan-1-one (Darocure 1116, available from Merck Co.); 2-hydroxy-2-methyl-1-phenyl-propan-1-one (Darocure 1173, available from Merck Co.) and so on.

The present invention is described in more detail by referring to Examples and Comparative Examples.

FIG. 1 illustrates an example of the ink jet recording head to which the treating agent of the present invention is applied.

In the FIG., 1 is a head applied with the ink-repellent treatment, 2 an orifice for ejecting ink, 3 a thin layer comprising the ink-repellent agent coated by a means such as transfer, etc. on the head surface, 4 a substrate or constituting the head which is formed of a glass or silicon, etc.

Heaters which are generating elements for ejecting ink are patterned by sputtering, etc., on the substrate 4.

5 is a resin wall for formation of a nozzle, which is prepared into a predetermined shape by exposure development of a photosensitive resin.

6 is a glass plate, which is plastered onto the nozzle wall 5. The glass plate 6 is provided with the common ink chamber 7 for performing smoothly ink supply.

8 is a filter, bound to an ink supplying member (not shown), which is a portion for supplying ink to the head.

Figure 2:
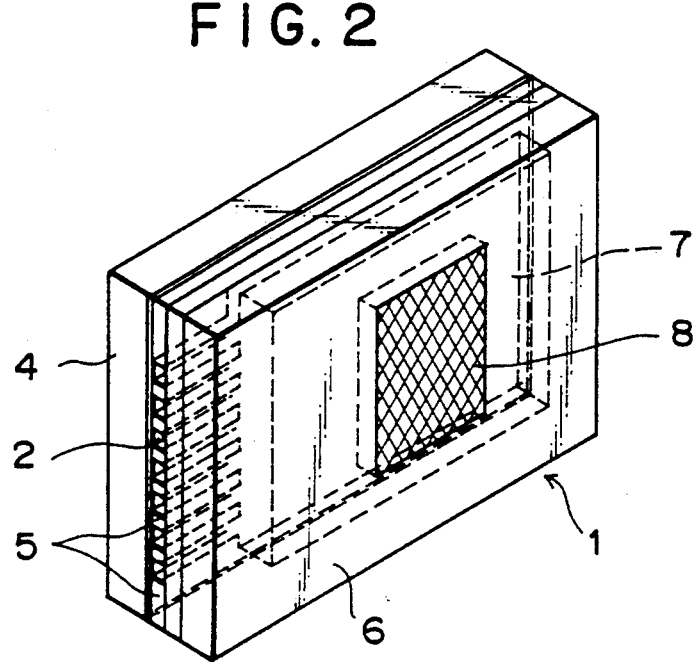
FIG. 2 is a perspective view showing the state of a head before coating of the ink-repellent agent.

FIG. 2 illustrates the state of the head before effecting the ink-repellent treatment, and the same symbols indicate the same names as in FIG. 1.

Figure 3:
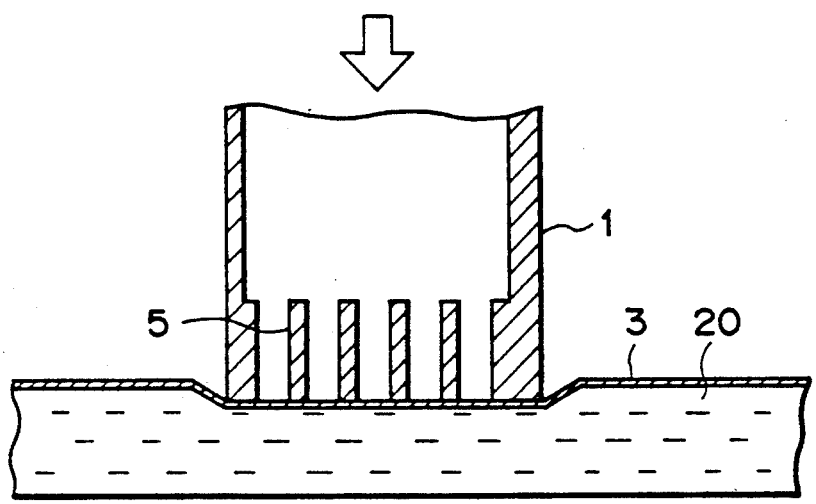
FIG. 3 is a schematic illustration of the transfer system which is an example of the coating method of the ink-repellent agent of the present invention.

FIG. 3 illustrates the transfer method which is an example of the method of using the ink-repellent agent of the present invention.

20 is a support (transfer plate), and it is a silicone rubber plate which is an elastic member. On its surface is formed the thin layer 3 comprising the ink-repellent agent. By pressing the head 1 by applying a certain load from above on the support 20, and then returning again to above, the thin layer 3 is transferred onto the surface of the head 1.

The thin layer has a thickness suitably of from 0.05 to 5 μm preferably 0.1 to 3 μm.

Figure 4:
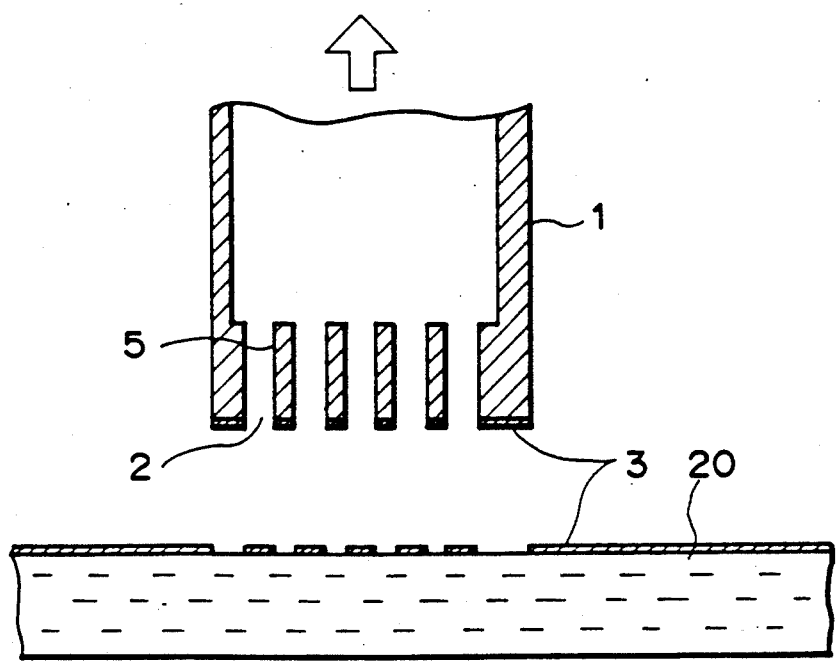
FIG. 4 is a perspective view showing the state after coating of the ink-repellent agent used in the present invention.

FIG. 4 shows the state after the head 1 was raised upward after completion of the step in FIG. 3, and the thin layer 3 comprising the ink repellent agent coated on the surface of the support 20 is transferred onto the head end surface, and the thin layer 3 does not transferred on the portion of the orifice 2 because no load is applied. In the head treated according to such means, various tests were conducted about durability of thin layer and softening characteristic by head in the following Examples.

EXAMPLE 1

First, a head shown in FIG. 2 was prepared, and the head was washed with MEK (methyl ethyl ketone) and Daifuron (Daikin Kogyo KK, trade name) so that the peripheral portion of the eject opening was washed and then dried.

On the other hand, silicone rubber was used as the support (transfer plate). As the ink-repellent agent, following compounds are used. These compounds were dissolved in a 1% solution of Daifuron and coated on the support to form a thin film

| ink-repellent agent | compounds of the present invention | acryloyl oligomer |
| --- | --- | --- |
| 1-1 | A$_1$ (100 parts) | — |
| 1-2 | A$_1$ (60 parts) | B$_1$ (40 parts) |
| 1-3 | A$_2$ (100 parts) | — |
| 1-4 | A$_2$ (60 parts) | B$_2$ (40 parts) |
| 1-5 | A$_3$ (100 parts) | — |
| 1-6 | A$_3$ (60 parts) | B$_3$ (40 parts) |

A$_1$:

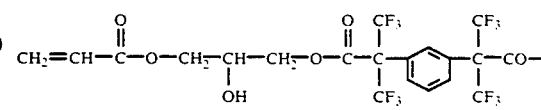

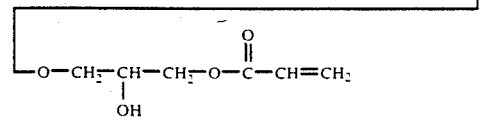

A$_2$: Compound (B-1), wherein X is a hydrogen atom
A$_3$: Compound (A-1), wherein X is a hydrogen atom
B$_1$: Acrylic acid ester of Epikote 828
B$_2$: Acrylic acid ester of pentaerythritol
B$_3$: Acrylic acid ester of Epikote 154
(B1 to B3 are acryloyl oligomers having no fluorine atom.)

As photo-initiators, 4 parts of 2-hydroxy-2-methyl-1-phenylpropan-1-one (Darocure 1173, available from Merck Co.) is added to the above.

In Comparative Example 1, fluoroalkylsilane (KP-801, available from Shinetsu Kagaku Co.) having the formula $C_8F_{17}C_2H_4SiNH_2$, and in Comparative Example 2, an acryl resin (Florocoat EC-104, available from Asahi Garasu Co.) having perfluoro alkyl group of an evaporation drying type are used, respectively, as an ink-repellent agent.

After evaporation of Daifuron which is the diluent of the ink-repellent agent, by pushing the heat 1 against the thin film on the support 20 as shown in FIG. 3 to transfer the thin film 3 thereon, the ink-repellent treatment of the head surface was effected.

After completion of the transfer as described above, the transferred thin film was UV cured by irradiation for 60 seconds with UV-light irradiation apparatus having a capacity of 50 mW/cm$^2$, then heated at a temperature of 150° C. to cure the treating agent by the reaction.

In case of Comparative Example 1, a heatcure treatment was carried out for 1 hour at 150° C., and in case of Comparative Example 2, a drying treatment was carried out for 30 minutes at 100° C. Thus, using each ink-repellent agent, the treating agent thin film layer 3 with substantially uniform thickness was bound firmly to the tip end surface of the head 1.

Next, the durability test of the ink-repellent agent was carried out.

Figure 5:
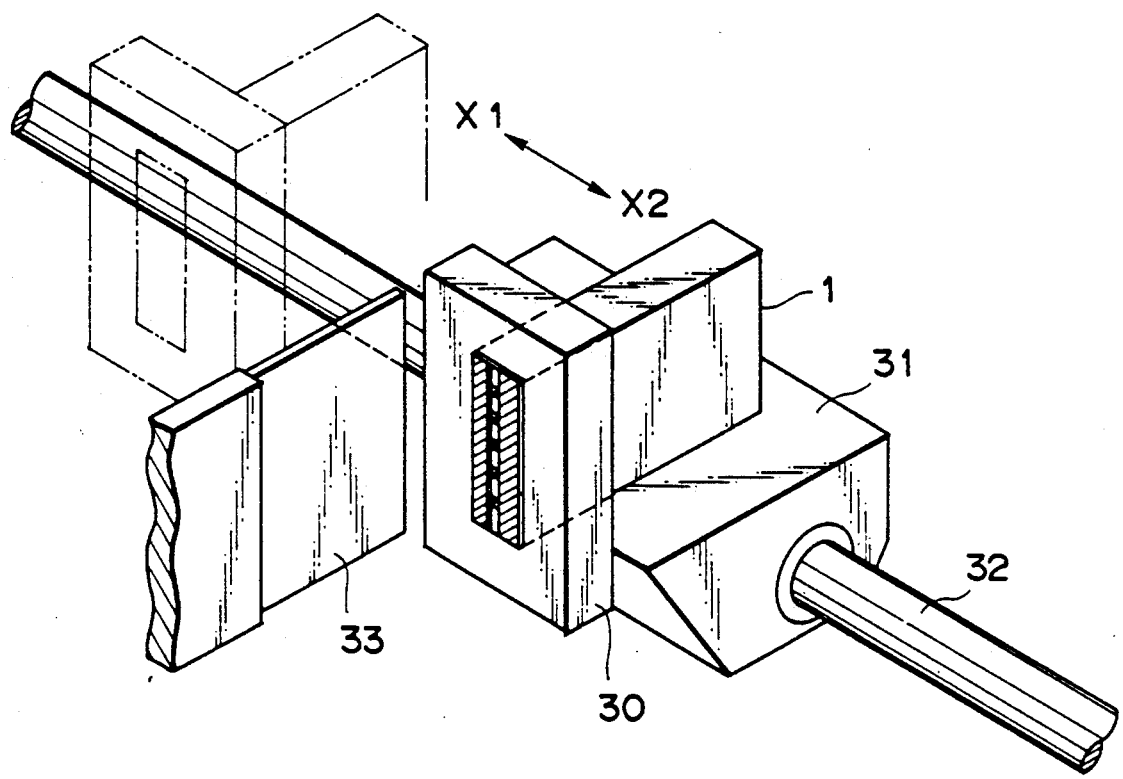
FIG. 5 is a schematic perspective view of the test method for testing durability of the head surface prepared according to the present invention.

The durability test was conducted in the form shown in FIG. 5 by reciprocal wiping of a silicone rubber with a thickness of 0.5 mm, while water was dropped so that the head surface was in the wetted conditions in any time.

In FIG. 5, 1 is a head, 30 a holder for holding the head, 31 a carriage of a printer on which the holder is mounted, 32 a shaft which enables movement of the carriage between the lateral directions $X_1$ and $X_2$. The carriage 31 is connected to a driving source (not shown), and is adapted so as to be movable between the left and right directions $X_1$ and $X_2$ of the carriage 31. 33 is a wiper blade made of a silicone rubber, and is fixed. The durability test was conducted by arranging the ink-repellent film formed on the surface of the head 1 so as to be contacted with the rubber blade 33. The contact width was made 1 mm.

The results are shown in the following Table:

| | Result of the durability test | |
|---|---|---|
| | Abrasion resistance | ink-repellent effect |
| Example 1-1 | OK for 250,000 times | no deterioration |
| Example 1-2 | OK for 250,000 times | no deterioration |
| Example 1-3 | OK for 250,000 times | no deterioration |
| Example 1-4 | OK for 250,000 times | no deterioration |
| Example 1-5 | OK for 250,000 times | no deterioration |
| Example 1-6 | OK for 250,000 times | no deterioration |
| Comparative Example 1 | becomes thin after ca. 30,000 times | deteriorated |
| Comparative Example 2 | becomes thin after ca. 10,000 times | deteriorated |

The ink-repellent agent according to the present invention was found to be excellent in abrasion resistance and ink-repellent property.

EXAMPLE 2

Using following ink-repellent agent, the durability tests were carried out similar with Example 1.

EXAMPLE 2-1

30 parts of Compound $A_1$ used in Example 1 and 70 parts of fluoroalkyl silane KP-801

EXAMPLE 2-2

30 parts of Compound $A_2$ used in Example 1 and 70 parts of Florocoat EC 104

The results are shown in the following Table.

| | Abrasion resistance | ink-repellent effect |
|---|---|---|
| Example 2-1 | OK for ca. 150,000 times | no deterioration |
| Example 2-2 | OK for ca. 100,000 times | no deterioration |

The ink-repellent agent according to the present invention was found to be good in abrasion resistance and ink-repellent property.

EXAMPLE 3

To 70 parts of compound (A-2) of the present invention having glycidyl groups at the end, 30 parts of tetrahydrophthalic acid anhydride and 1 part of benzyldimethylamine were added. The diluted mixture with Daifuron was coated on the ink jet head surface by means of the transfer method, with similar method in Example 1, followed by a heat treatment for 1 hour at 150° C. Thus, the ink jet head treated with the ink-repellent agent was prepared.

EXAMPLE 4

To 65 parts of compound (C-2) of the present invention having glycidyl groups at the end, 30 parts of Epikote 828 and 5 parts of bis[4-(diphenylsulfonyl) phenyl]-sulfide-bis-hexafluoro antimonate, as photocure catalyst, were mixed to form 1% solution of Daifuron. The surface of the ink jet head was coated by means of the transfer method using this solution with similar method in Example 1, followed by photocure treatment by irradiation for 60 seconds with UV-light irradiation apparatus having a capacity of 50 mW/cm$^2$. Thus, the ink jet head treated with the ink-repellent agent was prepared.

EXAMPLE 5

To 96 parts of compound $A_3$ used in Example 1, 4 parts of Darocure 1173 (2-hydroxy-2-methyl-1-phenylpropan-1-one (a product of Merck Co.) was added to form 1% solution of Daifuron. The surface of the ink jet head was coated by means of the transfer method using this solution with similar method in Example 1, followed by photocure treatment by irradiation for 60 seconds with UV-light irradiation apparatus having a capacity of 50 mW/cm$^2$. Thus, the ink jet head treated with the ink-repellent agent was prepared.

COMPARATIVE EXAMPLE 3

An ink jet head treated with the ink-repellent agent was prepared using 1% solution of KP801, perfluorosilicon type water-repellent agent, (a product of Shinetsu Kagaku Co.) with similar method in Example 1. Curing was carried out for 1 hour at 100° C.

The evaluation results of Examples 3, 4, 5 and Comparative Example 3 are shown in the following Table.

|  | Abrasion resistance | contact angle |
|---|---|---|
| Example 3 | OK for 250,000 times | 90° |
| Example 4 | OK for 250,000 times | 95° |
| Example 5 | OK for 250,000 times | 105° |
| Comparative Example 3 | becomes thin after ca. 30,000 times | 110° |

Figure 6:
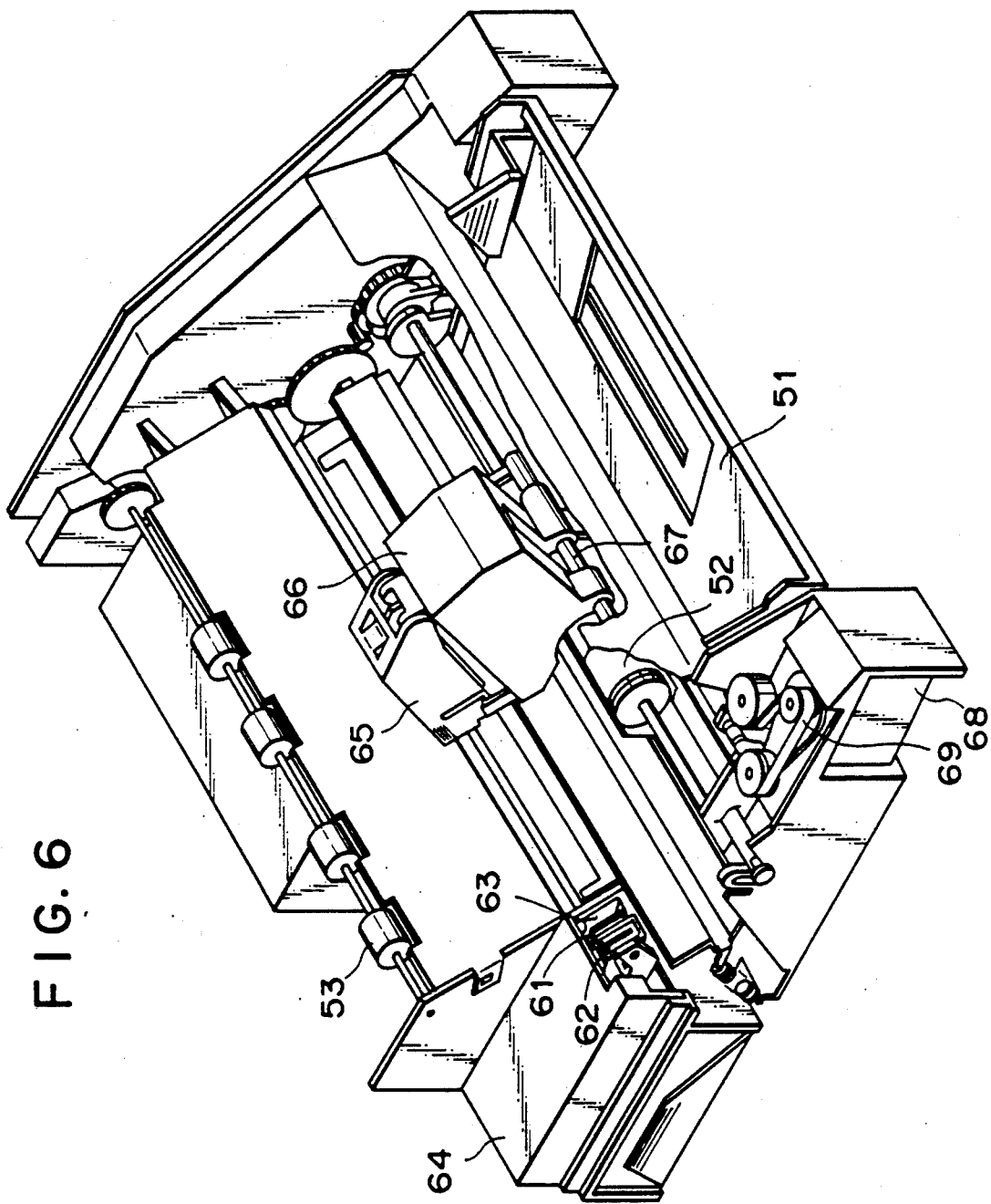
FIG. 6 is a perspective view showing an ink jet recording device equipped with the head for ink jet recording treated with the ink-repellent agent of the present invention.

FIG. 6 is a perspective view of an ink jet recording device equipped with the recording head subjected to the ink-repellent treatment of the present invention.

In FIG. 6, 61 is a blade as the wiping member, of which one end is held by a blade holding member to become a fixed end, assuming the form of a cantilever. The blade 61 is arranged at a position adjacent to the recording region by a recording head, and in the case of this example, is held in the form protruded in the course of the moving route of the recording head. 62 is a cap, provided with a constitution which performs capping in contact with the eject opening surface by being arranged at the home position adjacent to the blade 61 and moving in the direction vertical to the movement direction of the recording head. Further, 63 is an ink absorber provided adjacent to the blade 61, and is held in the form protruded in the course of the moving route of the recording head similarly as the blade 61. The eject restoration portion 64 is formed of the above blade 61, the cap 62 and the absorber 63, and removal of water, dust, etc. at the ink eject opening surface is performed with the blade 61 and the absorber 63.

65 is a recording head having an eject energy generating means, which performs recording by ejecting ink onto a recording medium opposed to the eject opening surface provided with an eject opening, and 66 is a carriage which moves the recording head 65 with the recording head 65 mounted thereon. The carriage 66 is engaged slidably with the guide shaft 67, and a part of the carriage 66 is connected (not shown) to the belt 69 driven by the motor 68. By this, the carriage 66 can be moved along the guide shaft 67, whereby movement of the recording region by the recording head 65 and the region adjacent thereto is rendered possible.

51 is a paper feeding portion for inserting the recording medium, and 52 is a paper delivery roller driven by a motor (not shown). With these constitutions, the recording medium is fed to the position opposed to the eject opening surface of a recording head, and ejected to the paper discharge portion arranged with a discharge roller 53 with the progress of recording.

In the constitution as described above, when the recording head 65 returns to the home position on completion of recording, etc., the cap 62 of the head restoration portion 64 is retreated from the moving route of the recording head 65, but blade 61 is protruded into the course of the moving route. As the result, the eject opening surface of the recording head 65 is wiped. When the cap 62 performs capping in contact with the eject opening of the recording head 65, the cap 62 moves so as to be protruded into the moving route of the recording head.

When the recording head 65 moves from the home position to the recording beginning position, the cap 62 and the blade 61 are at the same positions as during wiping as described above. As the result, also in such movement, the eject opening surface of the recording head 65 is wiped.

Movement of the recording head to the home position as described above is not limited only on completion of recording or during eject restoration, but movement to the home position occurs at predetermined intervals during movement of the recording head to the recording region for recording, and the above-mentioned wiping is performed as accompanied with such movement.

The recording head of the present invention is a head having On-demand type multi nozzles, which eject ink droplets by applying heat energy corresponding to recording signals, and are suitable for high speed recordings.

As described above, the ink-repellent agent of the present invention, in addition to use alone of the compounds of the present invention, by use thereof in a mixture with a liquid polymerizable compounds in general has such advantages as follows:

(1) improvement of abrasion resistance of thin layer by 5-fold or more as compared with that of the prior art;

(2) elevation of Tg of thin layer;

(3) no deterioration of the ink repellent effect of thin layer;

(4) no separation and precipitation by mixing at an adequate ratio during use;

(5) formation of uniform thin film, etc.

By the ink jet recording apparatus equipped with the head which is treated with the ink-repellent agent, it becomes possible to perform stable recordings for long period.

What is claimed is:

1. A head for ink jet recording comprising an end face including an ink eject opening having a thin layer of a polymer comprising a derivative compound of 1,3- or 1,4-bis(hexafluoroisopropyl) benzene, or 2,2-bisphenylhexafluoropropane represented by the formula (I) or (II):

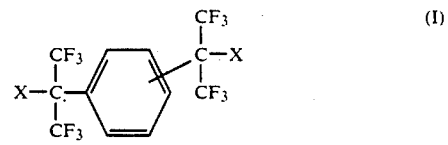

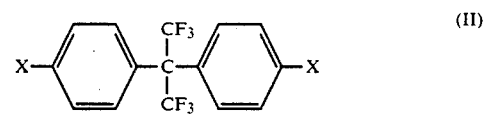

wherein X represents

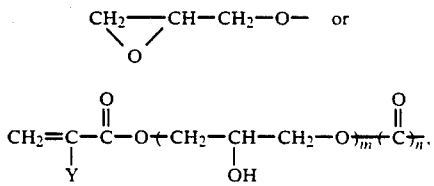

Y represents hydrogen atom or methyl group, m and n represent 0 or 1, and when m is 0, n is also 0.

2. The head for ink jet recording according to claim 1, wherein said polymer comprises a polymer of said derivative compound and a liquid compound polymerizable with said derivative compound.

3. The head for ink jet recording according to claim 2, wherein said liquid compound is a liquid epoxy compound or a liquid acrylic compound.

4. The head for ink jet recording according to claim 1, wherein said thin layer has a thickness of from 0.05 to 5 μm.

5. The head for ink jet recording according to claim 1, wherein said thin layer has a thickness of from 0.1 to 3 μm.

6. The head for ink jet recording according to claim 1, wherein said head is a head of On-demand type which ejects ink droplets by applying heat energy to ink.

7. The head for ink jet recording according to claim 1, wherein said derivative compound is one of the compounds represented by the formula (a) to (g):

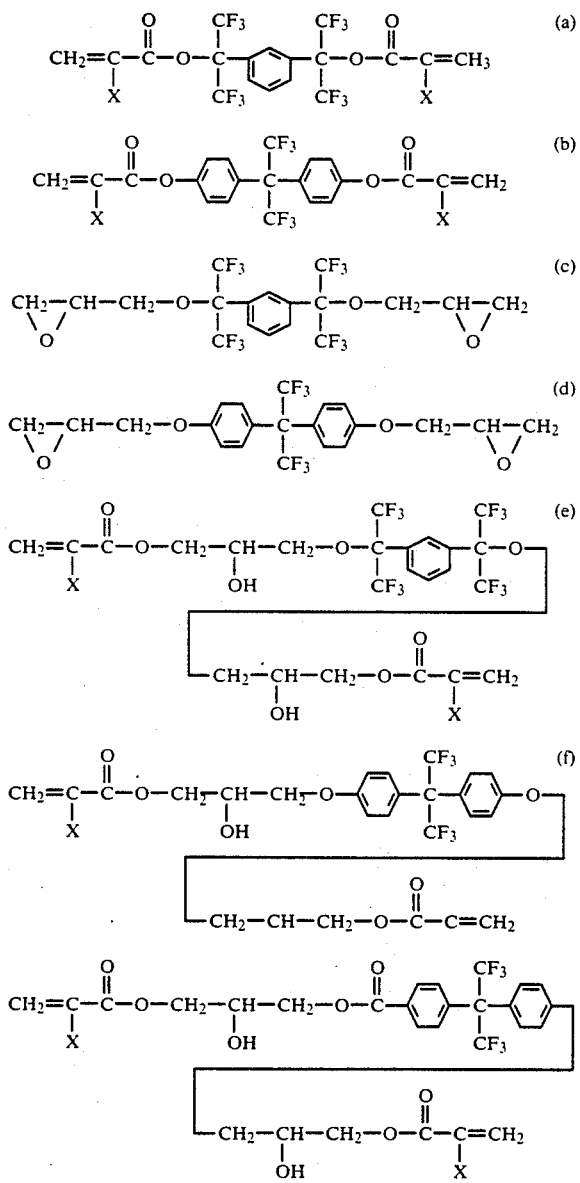

wherein X is hydrogen atom or methyl group.

8. An ink jet recording apparatus, having a recording head equipped therein, said recording head comprising an end face including an ink eject opening having a thin layer of a polymer comprising a derivative compound of 1,3-or 1,4-bis(hexafluoroisopropyl) benzene, or 2,2-bisphenylhexafluopropane represented by the formula (I) or (II):

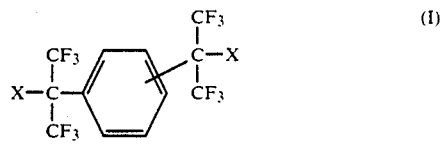

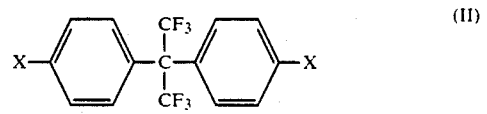

wherein X represents

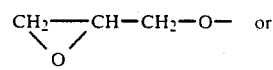

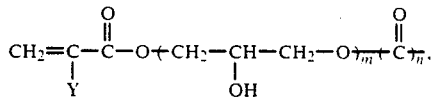

Y represents hydrogen atom or methyl group, m and n represent 0 or 1, and when m is 0, n is also 0.

9. The ink jet recording apparatus according to claim 8, wherein said polymer comprises a polymer of said derivative compound and a liquid compound polymerizable with said derivative compound.

10. The ink jet recording apparatus according to claim 8, wherein said liquid compound is a liquid epoxy compound or a liquid acrylic compound.

11. The ink jet recording apparatus according to claim 8, wherein said thin layer has a thickness of from 0.05 to 5μm.

12. The ink jet recording apparatus according to claim 8, wherein said thin layer has a thickness of from 0.1 to 3 μm.

13. The ink jet recording apparatus according to claim 8, wherein said head is a head of On-demand type which ejects ink droplets by applying heat energy to ink.

14. The ink jet recording apparatus according to claim 8, wherein said derivative compound is one of the compounds represented by the formula (a) to (g):

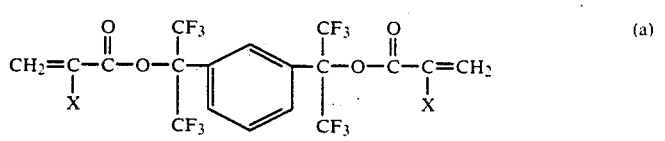

-continued
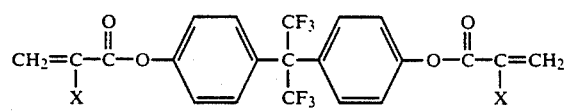
(b)
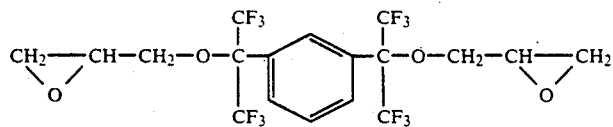
(c)
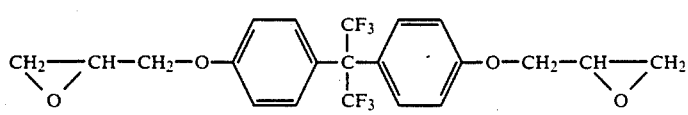
(d)
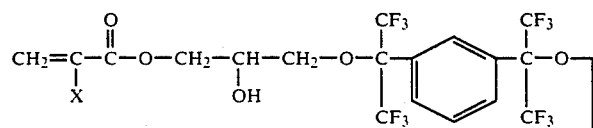
(e)
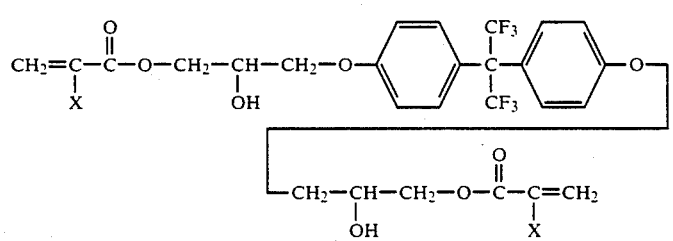
(f)
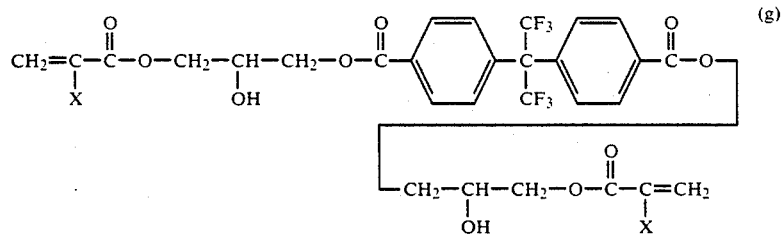
(g)
wherein X is hydrogen atom or methyl group.
* * * * *

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

Figure 7:
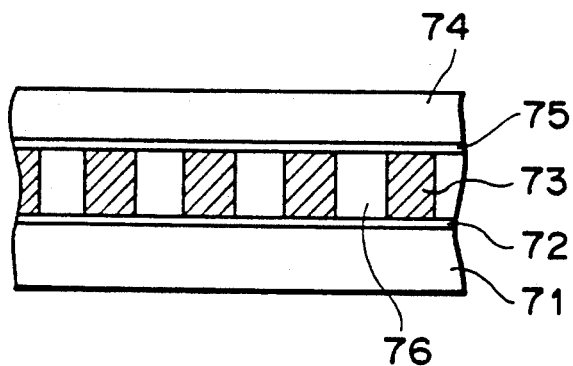
FIG. 7 is an illustration showing the constitution of a recording head of the prior art.
Figure 8A:
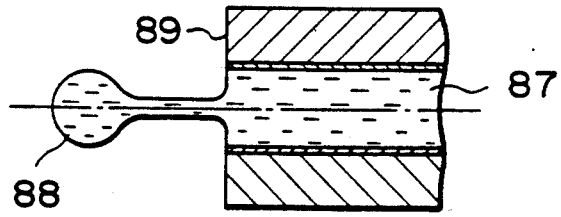
FIGS. 8A and 8B are illustrations showing the ejecting state of ink.
Figure 8B:
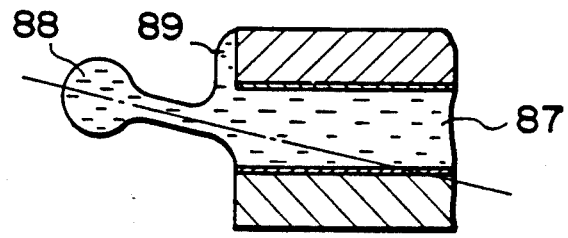

It is certified that error appears in the above-identified patent and that said Letters Patent is hereby corrected as shown below:

FIGURE 7:

Sheet 5, Figures 7, 8A and 8B should each be labeled --PRIOR ART--.

COLUMN 1:

Line 11, "head ink" should read --head for ink--.

Line 19, "developement" should read --development--.

Line 21, "processers" should read --processors--.

Line 33, "developements" should read --developments--.

Line 48, "example." should read --example,--.

Line 56, "jet" should be deleted.

Line 67, "ejecting" should read --eject--.

COLUMN 2:

Line 40, "connecting" should read --connected--.

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

Line 61, "desclosed" should read --disclosed--.

COLUMN 3:

Line 9, "dimenthylchlorosilane," should read --dimethylchlorosilane,--.

Line 28, "also," should read --Also,--; and "medium." should read -- medium,--.

Line 36, "surfaces" should read --surface--.

Line 40, "result" should read --result,--.

COLUMN 5:

Line 1, "above-derivative" should read --above derivative--.

Line 36, "compound" should read --a compound--.

Line 37, "OR" should read --or--.

COLUMN 6:

Line 35, in Formula (A-1), "$\overset{C}{\underset{X}{|}}$" should read --$\overset{C}{\underset{Y}{|}}$--

(both occurrences)

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

Line 42, In Formula (C-1), "$\overset{C}{\underset{X}{|}}$" should read --$\overset{C}{\underset{Y}{|}}$-- (both occurrences)

COLUMN 7:

Line 2, in Formula (A-3), "$\overset{C}{\underset{X}{|}}$" should read --$\overset{C}{\underset{Y}{|}}$-- (both occurrences)

Line 15, in Formula (C-3), "$\overset{C}{\underset{X}{|}}$" should read --$\overset{C}{\underset{Y}{|}}$-- (both occurrences)

Line 23, in Formula (B-1), "$\overset{C}{\underset{X}{|}}$" should read --$\overset{C}{\underset{Y}{|}}$-- (both occurrences)

Line 31, "X" should read --Y--.

Line 68, "2,2-bis(4 4-" should read --2,2-bis(4- --.

COLUMN 8:

Line 34, "cryalte." should read --crylate.--

Line 36, "hydoxyphenyl" should read --hydroxyphenyl--.

Line 68, "satisfactory." should read --satisfactorily.--

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

COLUMN 9:

Line 4, "of more" should read --or more--.

COLUMN 10:

Line 27, "dipentaerithritol" should read --dipentaerythritol--.

Line 48, "isocyanates" should read --isocyanate--.

Line 51, "alkylocrylates," should read --alkylacrylates,--.

Line 53, "examplified" should read --exemplified--.

COLUMN 11:

In Formula A-6, 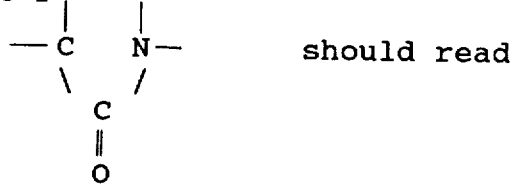 should read

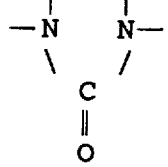

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

COLUMN 13:

Line 10, "lution" should read --lation-- and "do not cause." should read --are not caused.--.

Line 26, "surace" should read --surface--.

Line 31, "nitrils" should read --nitriles--.

Line 34, "acry-" should read --acryl- --.

COLUMN 14:

Line 29, "ink repellent" should read --ink-repellent--.

Line 32, "ferred" should read --fer--.

In Compound $A_1$, "
$$\begin{array}{c} -CO- \\ -O-CH_2- \end{array}$$
" should read
$$-- \begin{array}{c} -CO-O- \\ -CH_2- \end{array} --$$

COLUMN 15:

Line 3-4, insert heading between lines 3 and 4: --COMPARATIVE EXAMPLES 1 AND 2--.

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

COLUMN 16:

Line 53, "1-one (a" should read --1-one)(a--.

COLUMN 18:

Line 38, "hexafluopropane" should read --hexafluoro-propane--.

COLUMN 19:

Line 17, in Formula (a): "C|X" should read --C|Y-- (both occurrences); and "$CH_3$" should read --$CH_2$--.

Line 22, in Formula (b): "C|X" should read --C|Y-- (both occurrences)

Line 35, in Formula (e): "C|X" should read --C|Y-- (both occurrences)

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

Line 44, in Formula (f): 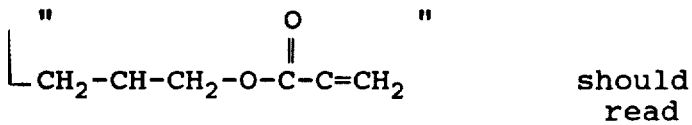

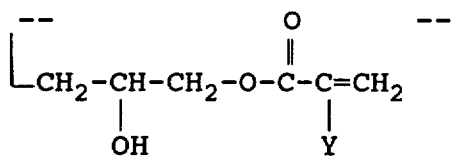   should read $$\left[ \begin{array}{c} -- \\ -CH_2-CH-CH_2-O-\overset{O}{\overset{\|}{C}}-C=CH_2 \\ | \quad\quad\quad | \\ OH \quad\quad\quad Y \end{array} \right. --$$

Line 52, insert --(g)-- and in the formula

"C"      should    --C--
 |        read      |
 X                     Y
(both occurrences)

COLUMN 20:

Line 1, "X" should read --Y--.

Line 7, "bisphenylhexafluopropane" should read --bisphenylhexafluoropropane--.

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

COLUMN 20:

Line 65, in Formula (a): "$\underset{X}{C}$" should read --$\underset{Y}{C}$-- (both occurrences)

COLUMN 21:

Line 2, in Formula (b): "$\underset{X}{C}$" should read --$\underset{Y}{C}$-- and (both occurrences)

Line 17, in Formula (e): "$\underset{X}{C}$" should read --$\underset{Y}{C}$-- (both occurrences)

Line 29, in Formula (f): "$\underset{X}{C}$" should read --$\underset{Y}{C}$-- (both occurrences)

UNITED STATES PATENT AND TRADEMARK OFFICE
CERTIFICATE OF CORRECTION

PATENT NO. : 5,043,747

DATED : August 27, 1991

INVENTOR(S) : Isao Ebisawa et al.

It is certified that error appears in the above-identified patent and that said Letters Patent is hereby corrected as shown below:

<u>COLUMN 21</u>:

Line 40, in Formula (g): "$\begin{array}{c}C\\|\\X\end{array}$" should read --$\begin{array}{c}C\\|\\Y\end{array}$--

(both occurrences)

Line 48, "X" should read --Y--.

Signed and Sealed this

Ninth Day of March, 1993

Attest:

STEPHEN G. KUNIN

*Attesting Officer*     *Acting Commissioner of Patents and Trademarks*